United States Patent [19]

Clement et al.

[11] Patent Number: 5,019,054
[45] Date of Patent: May 28, 1991

[54] MEDICAL DEVICE VALVING MECHANISM

[75] Inventors: Thomas P. Clement; David P. Weber, both of Bloomington, Ind.

[73] Assignee: Mectra Labs, Inc., Bloomington, Ind.

[21] Appl. No.: 432,084

[22] Filed: Nov. 6, 1989

[51] Int. Cl.$^5$ .............................................. A61M 5/00
[52] U.S. Cl. ...................................... 604/248; 604/32; 251/209; 251/309
[58] Field of Search ................. 604/32, 246, 248; 251/209, 231, 309, 312, 340; 137/595, 625.19, 625.23, 625.47, 626, 862; 433/95

[56] References Cited

U.S. PATENT DOCUMENTS

| | | | |
|---|---|---|---|
| 628,907 | 7/1899 | Hart | 251/309 |
| 786,215 | 3/1905 | Hepnar . | |
| 1,658,754 | 2/1928 | Wood . | |
| 3,012,752 | 12/1961 | Buck . | |
| 3,048,192 | 8/1962 | Murphy, Jr. . | |
| 3,788,602 | 1/1974 | Kitzie . | |
| 3,834,372 | 9/1974 | Turney . | |
| 3,957,082 | 5/1976 | Fuson et al. . | |
| 4,173,328 | 11/1979 | Karbo | 251/309 |
| 4,230,128 | 10/1980 | Aramayo . | |
| 4,282,873 | 8/1981 | Roth . | |
| 4,314,586 | 2/1982 | Folkman . | |
| 4,397,335 | 8/1983 | Doblar et al. . | |
| 4,540,156 | 9/1985 | Cross | 251/309 |
| 4,568,332 | 2/1986 | Shippert | 604/119 |
| 4,581,014 | 4/1986 | Millerd et al. . | |
| 4,593,717 | 6/1986 | Levasseur . | |
| 4,595,005 | 6/1986 | Jinotti . | |
| 4,645,496 | 2/1987 | Oscarsson . | |
| 4,648,868 | 3/1987 | Hardwick et al. . | |
| 4,667,927 | 5/1987 | Oscarsson | 251/309 |
| 4,807,666 | 2/1989 | Morse . | |
| 4,911,202 | 3/1990 | Nelson | 137/595 |
| 4,925,450 | 5/1990 | Imonti et al. | 604/248 |

FOREIGN PATENT DOCUMENTS

| | | | |
|---|---|---|---|
| 3528656 | 7/1986 | Fed. Rep. of Germany | 251/309 |
| 991478 | 5/1965 | United Kingdom | 251/309 |

*Primary Examiner*—Stephen C. Pellegrino
*Assistant Examiner*—Ralph A. Lewis
*Attorney, Agent, or Firm*—Barnes & Thornburg

[57] ABSTRACT

A medical device valving mechanism comprising a molded plastic, one-piece, elongated valve body molded to have a longitudinally extending body shaped to be gripped and securely held in either hand leaving the hand's thumb free for valve operational movement. The body has at least one fluid passageway extending longitudinally therethrough and a cylindrical opening extending transversely therethrough to intercept the at least one passageway. A cylindrical molded plastic, one-piece rotor for snug slidable and rotational insertion into the cylindrical opening to block the at least one passageway is provided. The rotor has at least one transaxial passageway which opens the at least one fluid passageway through the valve body when the rotor is in its valve opening position and which closes the at least one fluid passageway when the rotor is in its valve closing position. A thumb-actuated means is provided for rotating the rotor, the actuated means is disposed above the valve body and the rotor for convenient thumb movement.

20 Claims, 2 Drawing Sheets

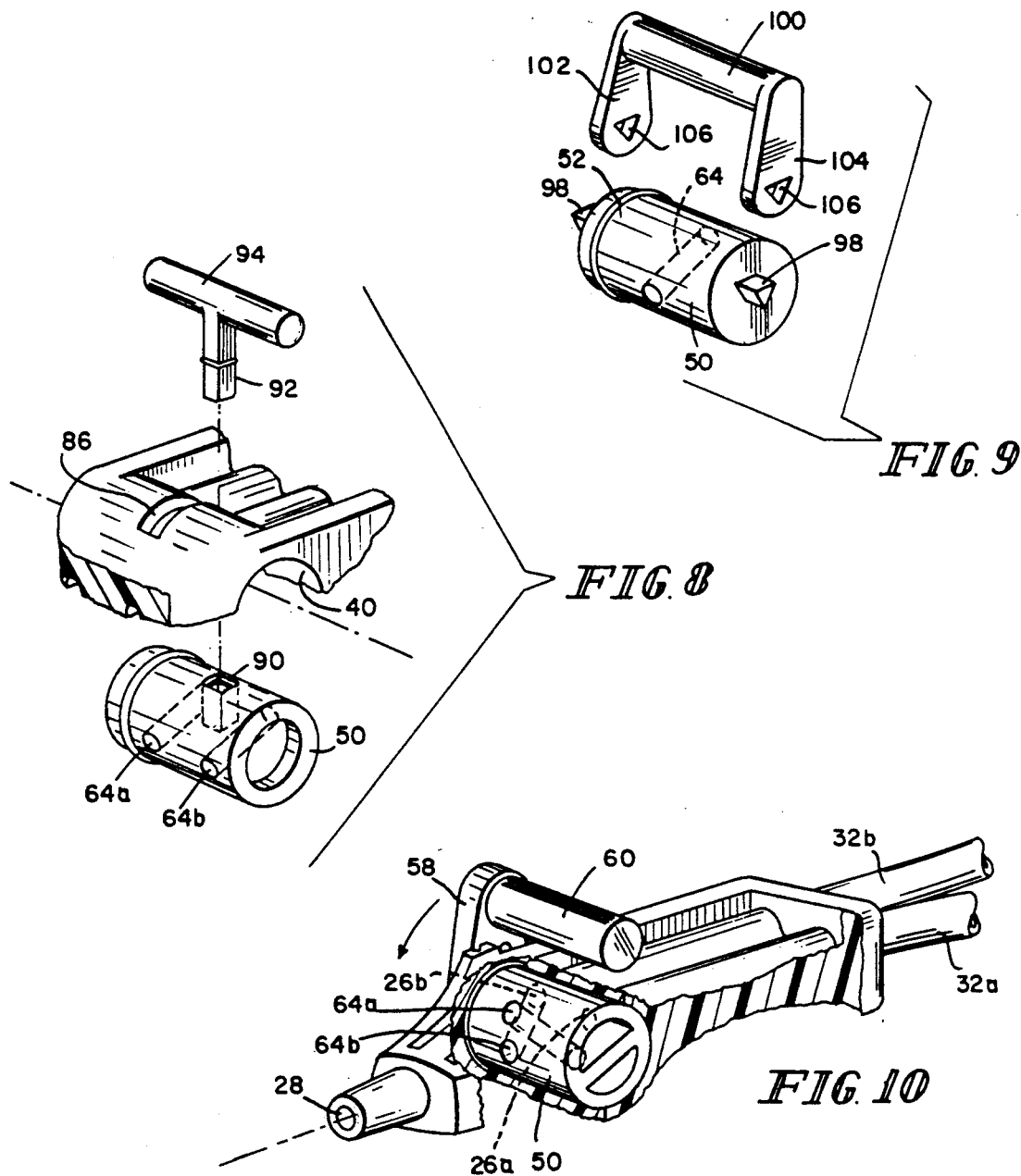

MEDICAL DEVICE VALVING MECHANISM

FIELD OF THE INVENTION

The present invention relates to medical device valving mechanisms and more particularly to the provision of a valve mechanism which may be held securely in one hand and operated by the thumb of that hand to open and close one or more valve passageways.

BACKGROUND OF THE INVENTION

In recent years, various types of medical procedures have been developed which involve the connection of various fluid tubes between the patient and various instruments including sources of fluid pumped into the patient and suction lines to remove fluid from the patient. All of this development activity has produced a need for a valving mechanism which can be securely held and controlled by one hand, leaving the other hand free to perform other functions. Since these mechanisms necessarily must be low-cost disposable mechanisms, the conventional prior art designs will not satisfy the requirements for several reasons. The prior art devices are usually too complex and costly to be thrown away when they are contaminated with body fluids. Also, the prior art devices are typically unwieldly and difficult to hold and control with one hand. An example of a prior art medical valve is shown in U.S. Pat. No. 4,568,332 issued to Ronald D. Shippert Feb. 4, 1986. The Shippert valve, which is designed for use in suction lipectomy, is made from metal and is fabricated from a multitude of parts which must be assembled together in a complex assembly system.

BRIEF DESCRIPTION OF THE INVENTION

The medical device valving mechanism of the present invention comprises a molded plastic, one-piece, elongated valve body molded to have a longitudinal extending body shaped to be gripped and securely held in either hand leaving the hand's thumb free for valve operational movement. The valve body provides at least one passageway extending longitudinal therethrough, and also provides a cylindrical opening or rotor bore extending transversely therethrough and intercepting the at least one passageway. A cylindrical molded plastic, one-piece rotor is provided for snug, slidable and rotational insertion into the cylindrical opening to block the said at least one passageway, the rotor being rotatable about its axis between valve opening and valve closing positions. The rotor has at least one transaxially extending passageway therethrough which opens the at least one fluid passageway through the valve body when the rotor is in its valve opening position and which closes the at least one fluid passageway when the rotor is in its valve closing position. The valving mechanism also comprises thumb-actuated means for rotating the rotor between its positions, the actuating means being disposed above the valve body and the rotor for convenient thumb movement of the rotor.

The valve body of the present invention is preferably molded to have a forward bottom portion shaped to be gripped by the index finger of one hand and a rearward bottom portion shaped to be gripped by the middle finger of the hand with a depending transverse bottom portion between the forward and rearward portions. The middle transverse bottom portion is preferably directly below the cylindrical opening which holds the rotor to be disposed partially between the index and middle finger for stabilization. Further, the rearward bottom portion is preferably transversely recessed to provide a comfortable gripping surface.

It is an object of the present invention, therefore, to provide a valving mechanism comprising primarily a molded, one-piece plastic valve body and a molded one-piece valve rotor for insertion into the body to complete the valving mechanism. It is another object of the present invention to provide such a mechanism which can be conveniently and comfortably held in one hand with the thumb of that one hand in position totally and positively to control the rotor of the mechanism.

It is another object of the present invention to provide such a valving mechanism having a valve body shaped to be securely held by the index and middle fingers with the valve rotor disposed in the space between the index and middle fingers for easy movement by the thumb.

Other objects and features of the present invention will become apparent as this description progresses.

BRIEF DESCRIPTION OF THE DRAWINGS

FIG. 8 shows an alternative rotor control means;

FIG. 9 shows another alternative rotor control means; and

FIG. 10 shows yet another embodiment.

DETAILED DESCRIPTION OF THE DRAWINGS

Figure 1:
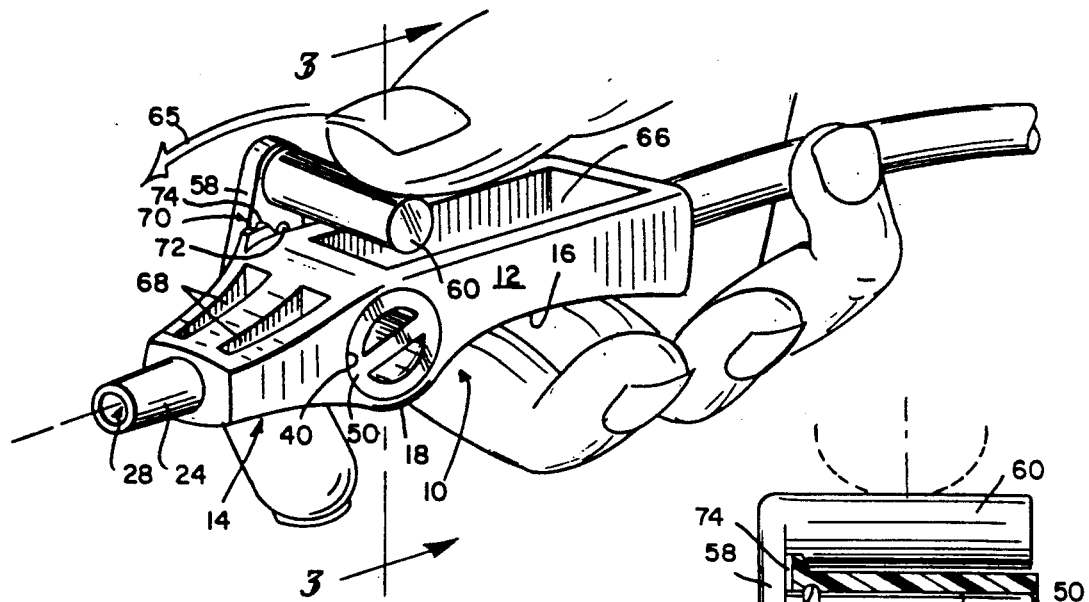
FIG. 1 is a perspective view of the valving mechanism of the present invention showing the mechanism held by one hand with the thumb of the hand controlling the valve rotor.
Figure 3:
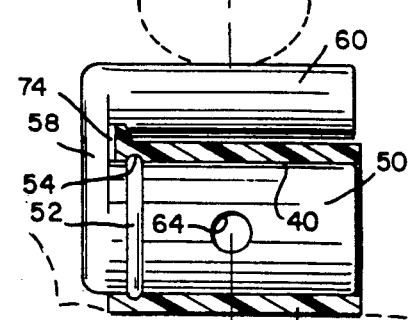
FIG. 3 is a sectional view taken along the lines 3—3 in FIG. 1.

A valving mechanism 10 in accordance with the present invention is shown in perspective view held by a right-hand in FIG. 1. In the drawings, and in this description, like reference numerals represent like parts. The illustrative mechanism 10 is shown comprising a valve body 12 which is illustrated as being a molded plastic, one-piece, elongated valve body molded to have a longitudinally extending body shaped to be gripped and securely held in either hand leaving the hand's thumb free for valve operational movement.

The illustrative valve body 12 is formed at its bottom surface to provide a forward bottom portion 14 shaped to be gripped by the index finger of one hand and a rearward bottom portion 16 shaped to be gripped by the middle finger and, depending upon the size of the hand, by the fourth finger of the hand, with a depending transverse bottom portion 18 between the forward and rearward portions 14, 16. It will be appreciated from the sectional view of FIG. 2 that the recessed portions 14, 16 are smoothly transversely recessed for gripping comfort while the depending central portion 18 is smoothly rounded to fit between the index and middle fingers. It will further be appreciated that, in this description and in the appended claims, statements such as "engaged by the index finger" and "engaged by the middle finger" are intended to indicate the general shape and size of an adult's hand relative to the mechanism 10 and that the body 12 is proportioned and shaped to be held generally by the index and middle fingers pressing the body against the palm of the hand, leaving the thumb free for movement to control the mechanism.

The valve body 12 is further provided with a forward nipple 24 and rearward nipple 26 to which vacuum lines or fluid lines of different types may be connected. These nipples 24, 26 are longitudinally aligned with a passageway 28 formed to extend longitudinally through the valve body 12 when the valve body is molded. The illustrative passageway 28, best seen in FIG. 2, includes a forward passageway portion 30 and a rearward passageway portion 32. In this description and in the appended claims, the term "at least one fluid passageway" is intended to define one or more passageways extending longitudinally through the valve body 12. It will be appreciated, as this description progresses, that the valve body may have, for instance, one, two or even three or more such passageways extending longitudinally therethrough and lying generally in the same plane such that their axes will generally intersect the axis of the valve rotor to be discussed hereinafter. It will further be appreciated that a valve body 12 may be formed to have, for instance, one forward passageway portion 30 and two parallel rearward passageways 32 which may be connected by the valve rotor to be described hereinafter. In summary, concerning the number of passageways, within the scope of the present invention, the valving mechanism 10 may be provided with one or more passageways therethrough and the passageways may be connected in different combinations by the movement of the rotor.

Figure 2:
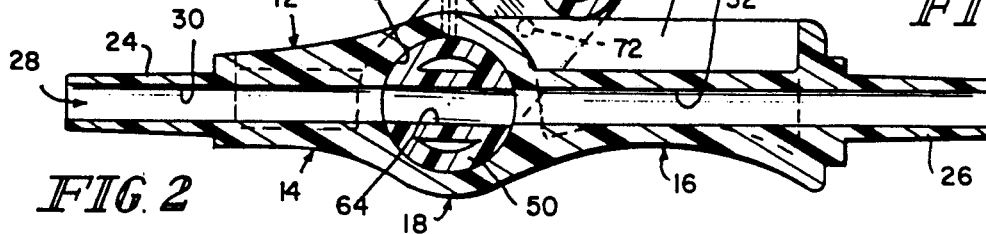
FIG. 2 is a longitudinal sectional view of the mechanism of FIG. 1.

The valve body 12 is molded to provide a cylindrical opening or bore 40 extending transversely through the valve body and illustratively, just above the central body portion 18 which is held between the index and middle fingers of the hand. This cylindrical opening 40 is positioned to intercept the passageway 28 through the valve body as best seen in FIG. 2. A cylindrical, molded plastic, one-piece rotor 50 is snugly and slidably rotatably inserted in the opening 40 to block the passageway 28 except when the rotor is in its passageway opening position.

The body 12 may preferably be molded from a fairly rigid material such as a polycarbonate plastic while the core 50 may preferably be molded from a softer plastic such as a polypropylene, nylon or teflon. The closeness of the snug fit of the rotor 50 in the bore 40 and the nature of the material from which the body 12 and rotor 50 are molded will determine the pressure capacity of the valving mechanism. It will be appreciated that a very snug rotor 50 fit in the bore 40 will accommodate high pressure. The rotor is provided with a peripherally extending ridge 52 integrally molded thereon to be snapped into a groove 54 formed in the bore 40 for the rotor.

Thus, when the softer plastic rotor 50 is inserted into the cylindrical opening or bore 40 so that the ridge 52 engages the groove 54, the valve rotor assembly will be fixed in the valve body 12 to complete the valving mechanism of the illustrative embodiment of FIG. 1. This very simple and easy assembly process is extremely attractive from an assembly cost point of view and from an operational point of view. In the illustrative embodiments of FIGS. 1-6, the rotor 50 is integrally molded and formed to have a one-piece thumb-actuated means for rotating the rotor. That is, as best illustrated in the drawings, the rotor 50 is molded to have a radially upwardly extending connecting portion 58 and a thumb engaging portion 60 extending generally parallel to and above the rotor 50. This engaging portion 60 may be serrated as indicated at 62 to provide a gripping surface for the thumb.

In FIGS. 1-4, the illustrative rotor 50 is provided with a single transaxially extending passageway 64 which is shown in alignment with the passageway portions 30, 32 in FIG. 2. When the rotor is rotated, however, the passageway 28 and its portions 30, 32 will be blocked by the rotor 50. Thus, the rotor 50 rotates between its valve opening position shown in FIG. 2 and a valve closing position 45° removed from that shown in FIG. 2. It will be appreciated that the valve rotor 50 may be moved to its closing position simply by pushing forwardly on the thumb engaging portion 60 as suggested by the arrow 65 in FIG. 1. The valve body 12 may be molded in a conventional fashion to have cavities such as illustrated at 66 and 68 to use less plastic material and to make the valve body lighter and easier to hold. It will also be appreciated that the valve body 12 may be formed with detent means indicated at 70 which will give the medical personnel a feeling for when the rotor 50 is in its desired position. A detent means 70 may include, for instance, a protrusion 72 on the connecting portion 58 of the rotor which must move past a resilient protrusion 74 on the valve body.

Figures 4, 5, 6:
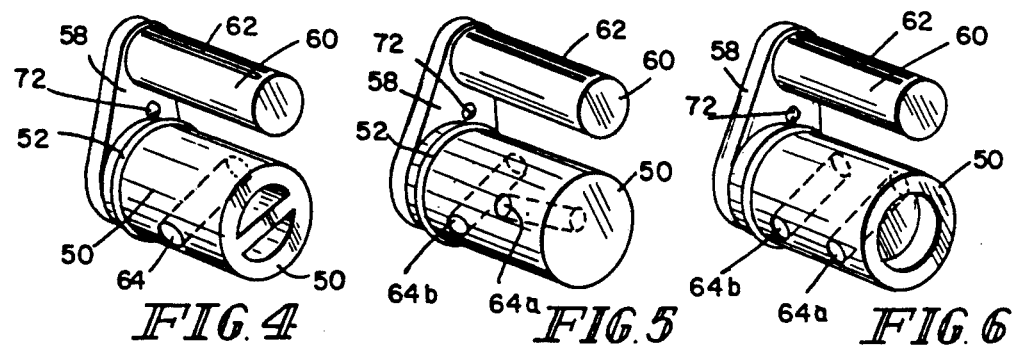
FIGS. 4, 5 and 6 are perspective views of various rotor bodies for the mechanism of FIG. 1.

Referring further to FIGS. 4, 5 and 6, it will be seen that, while FIG. 4 shows a single passageway 64 in the valve rotor 50, FIG. 5 shows transversely spaced apart passageways 64a and 64b which are 90° spaced apart. It will further be seen that FIG. 6 shows two transversely spaced apart passageways 64a and 64b formed in the rotor 50 to accommodate two parallel passageways through the valve body 12. It will be appreciated that, within the scope of this invention, there may be a wide variety of combinations of passageways 64a, 64b with the passageways arranged to open and close the passageways 28a, 28b at various rotor 50 positions. The passageways 28a, 28b may be opened and closed together or alternately opened and closed. The valve positions of the rotor 50 may be selected to be 45° apart or 90° apart or any selected angle sufficient to provide full closing and opening.

Figure 7:
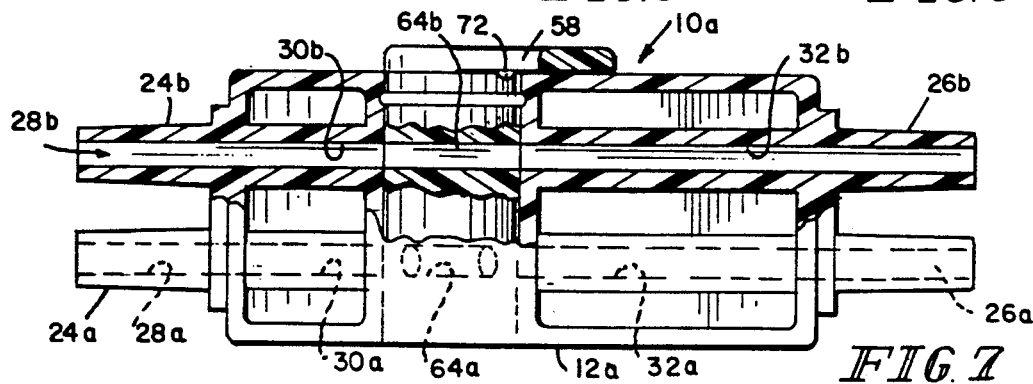
FIG. 7 is a longitudinal sectional view of a different embodiment showing two separate passageways through the valve, both controlled by a valve rotor.

Referring then to FIG. 7, it will be seen that there is illustrated a valving mechanism 10a having a valve body 12a formed to include parallel, side by side, longitudinally extending passageways 28a and 28b. These passageways 28a, 28b are formed to have the forward portions 30a, 30b and rearward portions 32a, 32b connecting, respectively, the forward nipples 24a, 24b and the rearward nipples 26a, 26b. When a rotor such as that illustrated in FIG. 5 is inserted into the valve body 12a of FIG. 7, the passageway 28a is open when the passageway 28b is closed and vice versa. When the rotor assembly of FIG. 6, however, is inserted into the valve body 12a, both passageways 28a, 28b are opened and closed by the same movement of the rotor 50.

In FIG. 8, there is illustrated a valve body having an elongated slot 86 just above the rotor 50, and the rotor 50 is illustrated as having an opening 90 therein for receiving a stem 92 which extends downwardly through the slot 86 to provide a driving connection for the rotor 50. The upper end of this stem 92 carries a crossbar 94 or thumb engaging portion. In the embodiment of FIG. 8, for instance, the stem 92 may be designed to snap into the opening 90 to make a permanent connection between the stem and the rotor 50.

Referring to FIG. 9, it will be seen that another approach for providing a driving connection between the operator's thumb and the rotor 50 is illustrated. In the FIG. 9 structure, the axially outer ends of the rotor 50 are provided with first engaging means 98. A saddle bar 100 is provided for thumb engagement, the saddle bar having depending sides 102, 104 which are formed to provide second engaging means 106 at the lower ends. Illustratively, the first engaging means 98 are male connectors which snap inwardly into the triangularly shaped female connectors of engaging means 106.

Referring to FIG. 10, still another embodiment is shown. In the FIG. 10 embodiment, the valve body has two input passageways 32a, 32b, but only one output passageway 28. (Again, like reference numbers represent like parts.) The rotor 50 in the FIG. 10 embodiment is designed to connect the passageways 26a, 26b alternatively to the passageway 28. Specifically, the passageways 64a, 64b in the rotor 50 connect the passageways 26a, 26b to the passageway 28 depending upon the position of the rotor.

The present invention, therefore, provides a two-piece, disposable, plastic stopcock handle-valve or valving mechanism which can be held and operated by either hand. The body of the handle-valve has a contoured bottom surface that fits into enough of the palm side of either hand of the operator, starting with the index finger, to permit the operator to both operate the handle-valve and direct its motion. Importantly, for control purposes, the thumb engages an actuating means which is preferably disposed axially and longitudinally just above the rotor of the valve, and this actuating or engaging portion may be integrally molded with the rotor. For control purposes, the connecting portion 58 of the rotor assembly may have a moment-arm of approximately one inch and a stroke of approximately three-fourths inch, a comfortable span for either an adult female or male hand. The top extension of the thumb engaging portion may be serrated to facilitate its movement by the thumb and the bottom or other surfaces of the valve body may be serrated at convenient locations to provide a convenient and comfortable grip. The valve body 12 and the core 50 are assembled with a slight interference fit to provide a good seal between the body and the core without requiring extreme pressure in excess of that which is comfortable for an adult female or male to move by thumb action.

What is claimed is:

1. A medical device valving mechanism comprising a molded plastic, one-piece, elongated valve body molded to have a longitudinally extending body shaped to be gripped and securely held in a user's hand leaving the hand's thumb free for valve operational movement, said body providing at least one fluid passageway extending longitudinally therethrough, said body also providing a cylindrical opening extending transversely therethrough and intercepting said at least one passageway, a cylindrical molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, thumb-actuated means connected to said rotor for rotating said rotor, said actuated means being disposed above said valve body and said rotor for convenient thumb movement of said rotor, and wherein the shaped body is to be gripped and held by fingers of the user's hand at points located on the shaped body below an upstream and a downstream side of the rotor with the fingers of the user's hand being located below the thumb-actuated means so as to provide the free thumb for valve operational movement.

2. The mechanism of claim 1 in which said thumb-actuated means is a plastic actuator integrally molded with said rotor to have a connecting portion extending radially upwardly from said rotor and a thumb engaging portion extending from said connecting portion transaxially above said valve body over said rotor.

3. The mechanism of claim 1 in which said thumb-actuated means includes a molded-plastic saddle bar extending transversely across said valve body above said rotor with integrally formed side bars depending from said saddle bar ends and drivingly connected to said rotor.

4. The mechanism of claim 1 in which said rotor is molded to have a peripherally extending ridge on its outer cylindrical surface and said valve body is formed to have a corresponding peripherally extending groove in said cylindrical opening surface, said ridge snapping into said groove to secure said rotor in said valve body for rotation and against radial movement.

5. A medical device valving mechanism comprising a molded plastic, one-piece, elongated valve body molded to have a longitudinally extending body shaped to be gripped and securely held in a users hand leaving the hand's thumb free for valve operational movement, said body providing at least one fluid passageway extending longitudinally therethrough, said body also providing a cylindrical opening extending transversely therethrough and intercepting said at least one passageway, a cylindrical molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, thumb-actuated means connected to said rotor for rotating said rotor, said actuated means being disposed above said valve body and said rotor for convenient thumb movement of said rotor, wherein said valve body is molded to have a forward bottom portion shaped to be gripped by the index finger of one hand and a rearward bottom portion shaped to be gripped by the middle finger of the hand with a depending transverse bottom portion between said forward and rearward portions, said transverse bottom portion being directly below said cylindrical opening which holds said rotor to be disposed partially between the index and middle fingers for stabilization with the fingers holding the body against the palm of the hand.

6. The mechanism of claim 5 in which said rearward bottom portion is transversely recessed to provide a comfortable gripping surface.

7. The mechanism of claim 6 in which said thumb-actuated means is a plastic actuator integrally molded with said rotor to have a connecting portion extending radially upwardly from said rotor and a thumb engaging portion extending from said connecting portion transaxially above said valve body over said rotor.

8. The mechanism of claim 5 in which said thumb-actuated means is a plastic actuator integrally molded with said rotor to have a connecting portion extending radially upwardly from said rotor and a thumb engaging portion extending from said connecting portion transaxially above said valve body over said rotor.

9. A medical device valving mechanism comprising a molded plastic, one-piece, elongated valve body molded to have a longitudinally extending body shaped to be gripped and securely held in a uses hand leaving the hand's thumb free for valve operational movement, said body providing at least one fluid passageway extending longitudinally therethrough, said body also providing a cylindrical opening extending transversely therethrough and intercepting said at least one passageway, a cylindrical molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, thumb-actuated means connected to said rotor for rotating said rotor, said actuated means being disposed above said valve body and said rotor for convenient thumb movement of said rotor, wherein said valve body is provided with an access opening above said cylindrical opening for said rotor, said thumb-actuated means including a stem portion extending downwardly through said access opening drivingly to engage said rotor.

10. A medical device valving mechanism comprising a molded plastic, one-piece, elongated valve body molded to have a longitudinally extending body shaped to be gripped and securely held in a users hand leaving the hand's thumb free for valve operational movement, said body providing at least one fluid passageway extending longitudinally therethrough, said body also providing a cylindrical opening extending transversely therethrough and intercepting said at least one passageway, a cylindrical molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, thumb-actuated means connected to said rotor for rotating said rotor, said actuated means being disposed above said valve body and said rotor for convenient thumb movement of said rotor, wherein said thumb-actuated means includes a molded-plastic saddle bar extending transversely across said valve body above said rotor with integrally formed side bars depending from said saddle bar ends and drivingly connected to said rotor, the side bars are drivingly connected through first engaging means on opposite ends of the rotor which extend outwardly from said valve body and wherein said side bars are provided with second engagement means for snapping engagement respectively with said first engagement means.

11. A valve mechanism comprising a valve body molded from a single piece of plastic to have a longitudinally extending gripping body providing a bottom forward surface transversely recessed to be engaged by the index finger and a bottom rearward surface transversely recessed to be engaged by the middle finger such that said body can be securely held in one hand leaving the thumb of the hand free for operational movement, said valve body further having a central portion disposed between said forward and rearward portions to extend transversely across and downwardly between said forward and rearward recessed surfaces, at least one fluid passageway extending longitudinally through said valve body, and a cylindrical opening extending transaxially through said central body portion to intercept said at least one fluid passageway, and a cylindrical, molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway when said rotor is in said valve opening position and which closes said at least one passageway when said rotor is in said valve closing position, and thumb-actuated means connected to said rotor for rotating said rotor.

12. A valve mechanism comprising a valve body molded from a single piece of plastic to have a longitudinally extending gripping body providing a bottom forward surface transversely recessed to be engaged by the index finger and a bottom rearward surface transversely recessed to be engaged by the middle finger such that said body can be securely held in one hand leaving the thumb of the hand free for operational movement, said valve body further having a central portion disposed between said forward and rearward portions to extend transversely across and downwardly between said forward and rearward recesses surfaces, at least one fluid passageway extending longitudinally through said valve body, and a cylindrical opening extending transaxially through said central body portion to intercept said at least one fluid passageway, and a cylindrical, molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway when said rotor is in said valve opening position and which closes said at least one passageway when said rotor is in said valve closing position, and thumb-actuated means connected to said rotor for rotating said rotor wherein said rotor is molded to have a peripherally extending ridge on its outer cylindrical surface and said valve body is formed to have a corresponding peripherally extending groove in said cylindrical opening surface, said ridge snapping into said groove to secure said rotor in said valve body for rotation and against axial movement.

13. A medical device valving mechanism comprising a molded plastic, one-piece, elongated valve body molded to have a longitudinally extending body shaped to be gripped and securely held in either hand leaving the hand's thumb free for valve operational movement, said body being molded to have at least two passageways extending longitudinally therethrough, said passageways being generally parallel and having axes lying generally in the same plane, said body also providing a cylindrical opening extending transversely therethrough and intercepting said at least two passageways with said opening having an axis generally perpendicular to the axes of said valve body passageways and generally parallel to said plane of said passageway axes, a cylindrical molded plastic, one-piece rotor for snug slidable and rotational insertion into said cylindrical opening to block said at least two passageways, said rotor being rotatable about its axes selectively to open and close said passageways, said rotor having transaxially extending passageways therethrough corresponding to the at least two passageways through said valve body to open and close said valve body passageways, said rotor passageways being spaced along the axis of said rotor, and thumb-actuated means connected to said rotor for rotating said rotor, said actuated means being disposed above said valve body and said rotor for convenient thumb movement of said rotor.

14. A disposable throw-away hand held medical device valving mechanism comprising a molded plastic, one-piece, elongated valve body molded to have a longitudinally extending body shaped to be gripped and securely held in a users hand leaving the hand's thumb free for valve operational movement, said body providing at least one fluid passageway extending longitudinally therethrough, said body also providing a cylindrical opening extending transversely therethrough and intercepting said at least one passageway, a cylindrical molded plastic, one-piece rotor for snug slidable and rotational insertion into said cylindrical opening to block said at least one passageway, said rotor being rotatable between valve opening and valve closing positions, said rotor having at least one transaxial passageway therethrough which opens said at least one fluid passageway through said valve body when said rotor is in said valve opening position and which closes said at least one fluid passageway when said rotor is in said valve closing position, thumb-actuated means connected to said rotor for rotating said rotor, said actuated means being disposed above said valve body and said rotor for convenient thumb movement of said rotor, and wherein the shaped body is to be gripped and held by fingers of the user's hand at points located on the shaped body so as to provide the free thumb for valve operational movement.

15. The mechanism of claim 14 in which said thumb-actuated means is a plastic actuator integrally molded with said rotor to have a connecting portion extending radially upwardly from said rotor and a thumb engaging portion extending from said connecting portion transaxially above said valve body over said rotor.

16. The mechanism of claim 15 in which said rotor is molded to have a peripherally extending ridge on its outer cylindrical surface and said valve body is formed to have a corresponding peripherally extending groove in said cylindrical opening surface, said ridge snapping into said groove to secure said rotor in said valve body for rotation and against axial movement.

17. The mechanism of claim 14 in which said valve body is provided with an access opening above said cylindrical opening for said rotor, said thumb-actuated means including a stem portion extending downwardly through said access opening drivingly to engage said rotor.

18. The mechanism of claim 14 in which said thumb-actuated means includes a molded-plastic saddle bar extending transversely across said valve body above said rotor with integrally formed side bars depending from said saddle bar ends and drivingly connected to said rotor.

19. The mechanism of claim 18 in which said rotor is provided with first engaging means on opposite ends of the rotor which extend outwardly from said valve body and wherein said side bars are provided with second engagement means for snapping engagement respectively with said first engagement means.

20. The mechanism of claim 14 in which said rotor is molded to have a peripherally extending ridge on its outer cylindrical surface and said valve body is formed to have a corresponding peripherally extending groove in said cylindrical opening surface, said ridge snapping into said groove to secure said rotor in said valve body for rotation and against axial movement.

* * * * *